(12) United States Patent
Gerasimova et al.

(10) Patent No.: US 8,859,266 B2
(45) Date of Patent: Oct. 14, 2014

(54) BINARY PROBE SYSTEM FOR SENSITIVE DETECTION OF TARGET ANALYTES

(75) Inventors: Yuliva V. Gerasimova, Orlando, FL (US); Dmitry M. Kolpashchikov, Orlando, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 109 days.

(21) Appl. No.: 13/096,027

(22) Filed: Apr. 28, 2011

(65) Prior Publication Data

US 2011/0269129 A1 Nov. 3, 2011

Related U.S. Application Data

(60) Provisional application No. 61/328,791, filed on Apr. 28, 2010.

(51) Int. Cl.

| | | |
|---|---|---|
| C12M 1/34 | (2006.01) | |
| G01N 33/53 | (2006.01) | |
| C12Q 1/00 | (2006.01) | |
| C12P 19/34 | (2006.01) | |
| C12N 9/22 | (2006.01) | |
| B01L 3/00 | (2006.01) | |
| G01N 31/22 | (2006.01) | |
| C07H 21/02 | (2006.01) | |
| C07H 21/04 | (2006.01) | |
| C12Q 1/68 | (2006.01) | |

(52) U.S. Cl.
CPC .................. *C12Q 1/6823* (2013.01)
USPC ............. 435/287.2; 435/4; 435/6.1; 435/7.6; 435/91.1; 435/199; 422/430; 536/23.1; 536/24.3; 536/25.32

(58) Field of Classification Search
USPC ................... 435/4, 6.1, 7.6, 91.1, 199, 287.2; 422/430; 536/23.1, 24.3, 25.32
See application file for complete search history.

(56) References Cited

U.S. PATENT DOCUMENTS

| | | | |
|---|---|---|---|
| 2007/0231810 A1* | 10/2007 | Todd et al. | 435/6 |
| 2008/0044834 A1* | 2/2008 | Heyduk | 435/6 |
| 2009/0176318 A1 | 7/2009 | Kolpashchikov | |

FOREIGN PATENT DOCUMENTS

WO    WO2008/054834    *   5/2008

OTHER PUBLICATIONS

Kolpashchikov, A Binary Deoxyribozyme for Nucleic AcidAnalysis, 2007, ChemBioChem, 8, 2039-2042.*
F-substrate EcoRV restriction site, NEB Datasheet, down loaded from the internet,[ http://tools.neb.com/NEBcutter2/cutshow], 2013, printed on Feb. 21, 2013, p. 1.*
F-substrate stem loop structure, IdtDNA Datasheet, down loaded from the internet, [https://www.idtdna.com/Scitools/Applications], 2013, prineted on Feb. 21, 2013.*
Gerasimova et al, Enzyme-assisted binary probe for sensitive detection of RNA and DNA, 2010, Chem. Commun., 46, 8761-8763.*
Kolpashchikov, Dmitry M., "A Binary DNA Probe for Highly Specific Nucleic Acid Recognition", J. AM. Chem. Soc, 2006, vol. 128, pp. 10625-10628.
Kolpashchikov, Dmitry M. et al., "Boolean Control fo Aptamer Binding States", J. AM. Chem. Soc., 2005, vol. 127, pp. 11348-11351.

* cited by examiner

*Primary Examiner* — Narayan Bhat
(74) *Attorney, Agent, or Firm* — Timothy H. Van Dyke; Beusse, Wolter, Sanks & Maire, P.A.

(57) ABSTRACT

The present disclosure encompasses systems, and their methods of use, for detecting a target analyte. The systems include a first and second oligonucleotide probe that associate together to form a complex that binds to a target analyte; a cleavable reporter molecule that binds to the complex; and cleaving agent.

17 Claims, 8 Drawing Sheets

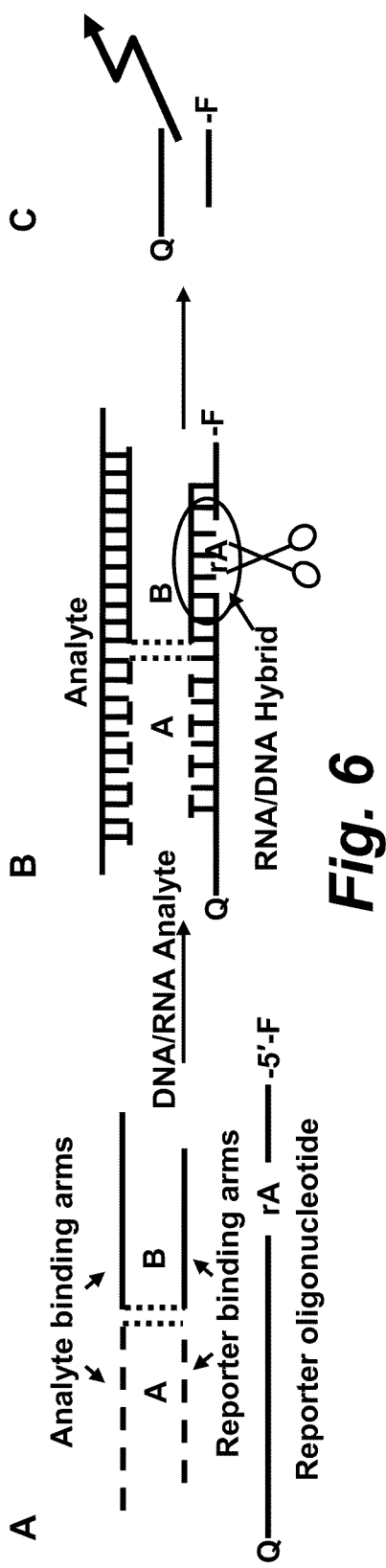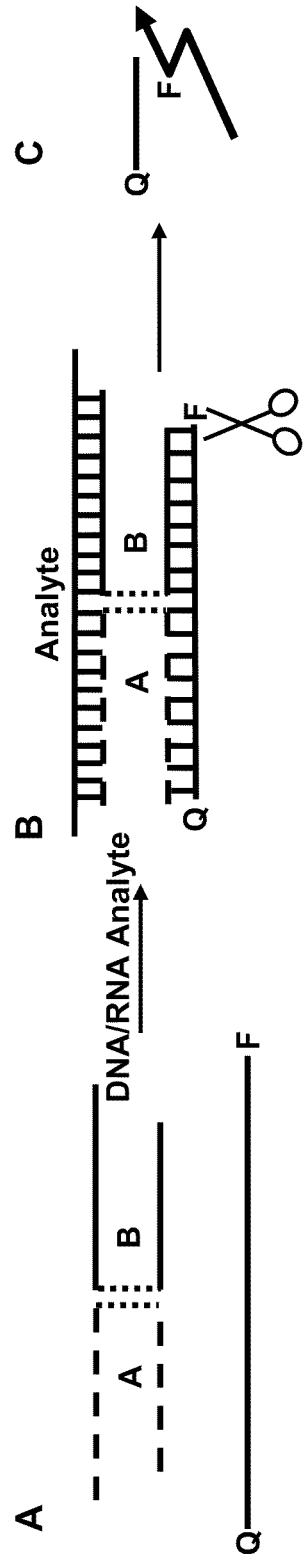

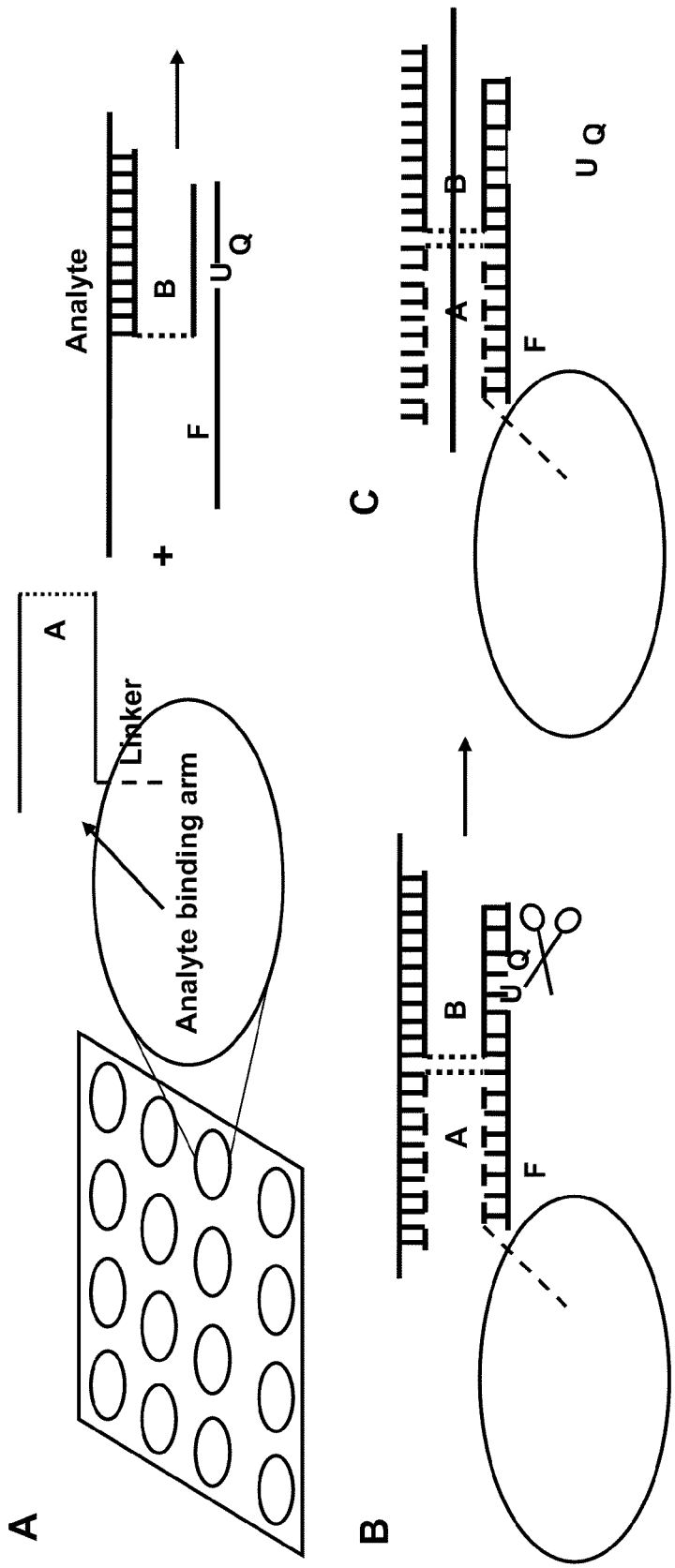
Fig. 10
Fig. 11

BINARY PROBE SYSTEM FOR SENSITIVE DETECTION OF TARGET ANALYTES

CROSS REFERENCE TO RELATED APPLICATION

This application claims priority to and benefit of U.S. Provisional Patent Application Ser. No. 61/328,791, filed on Apr. 28, 2010, which is incorporated herein by reference in its entirety.

STATEMENT REGARDING FEDERALLY SPONSORED RESEARCH OR DEVELOPMENT

This disclosure was made with government support under NIH Grant No. R21 HG004060 awarded by the U.S. National Institutes of Health of the United States government. The government has certain rights in the disclosure.

TECHNICAL FIELD

The present disclosure is generally related to systems for the detection of specific analytes using a binary probe and a reporter oligonucleotide.

BACKGROUND

Real time assays for the detection of specific nucleic acids are of great importance, since they enable instant detection of specific RNA/DNA sequences without the need of separating the probe-analyte hybrid from the unbound probe. Molecular beacon probes are a novel tool for real-time nucleic acid analysis (Tyagi & Kramer (1996) *Nat. Biotechnol.* 14: 303-308; Marras et al., (2006) *Clin. Chim. Acta.* 363: 48-60; Wang, et al., (2009) *Angew. Chem. Int. Ed. Engl.* 48: 856-870; Li et al., (2008) *Biochem. Biophys. Res. Commun.* 373: 457-461; Venkatesan et al., (2008) *Chem. Soc. Rev.* 37: 648-663).

The traditional molecular beacon is a stem-loop folded oligonucleotide with a fluorophore at the 5'-end and a quencher at its 3'-end. Hybridization to a complementary single-stranded DNA or RNA converts the molecular beacon into the elongated conformation, in which the fluorophore is remote from the quencher, resulting in high fluorescence. The simplicity and elegance of molecular beacon design has made this probe a popular tool for nucleic acid analysis and has served as an inspiration for a number of related assays (see, for example, Du et al., (2003) *J. Am. Chem. Soc.* 125: 4012-4013; Ye et al., (2004) *J. Am. Chem. Soc.* 126: 7740-7741; Liu & Lu (2006) *Methods Mol. Biol.* 335: 275-288; Grossmann et al., (2007) *Angew. Chem. Int. Ed. Engl.* 46: 5223-5225; Lin et al., (2008) *Nucleic Acids Res.* 36: e123).

Molecular beacon probes are extensively used in real-time PCR assays (Whitman & Dunbar (2008) *Recent Pat. DNA Gene Seq.* 2: 20-26) and for RNA monitoring in living cells (Bao et al., (2009) *Ann. Rev. Biomed. Eng.* 11: 25-47; Tyagi. S. (2009) *Nat. Methods* 6: 331-338). Importantly, the stem-loop structure not only brings the fluorophore close to the quencher but also improves the probe specificity. Molecular beacon probes discriminate between two nucleic acid sequences that differ by a single nucleotide in a wider temperature range than do linear hybridization probes (Bonnet et al., (1999) *Proc. Natl. Acad. Sci. USA.* 96: 6171-6176). These properties are of particular importance for single nucleotide polymorphism (SNP) genotyping.

One factor that limits the application of molecular beacon probes in SNP genotyping is their high synthetic cost. Chemical synthesis of a regular molecular beacon probe requires conjugation of an oligonucleotide with two organic dyes, a fluorophore and a quencher. Moreover, at least one round of HPLC purification is required to remove fluorescent impurities, which cause high background fluorescence and reduce both the sensitivity and the dynamic range of the probe. Taking into account that the analysis of each individual SNP requires two molecular beacon probes (each complementary to a specific allele), genotyping thousands of SNPs by molecular beacon probes becomes expensive. Accordingly, a binary approach for nucleic acid recognition (Kolpashchikov D. M. (2005) *J. Am. Chem. Soc.* 127: 12442-12443; Kolpashchikov D. M. (2006) *J. Am. Chem. Soc.*, 128: 10625-10628; Kolpashchikov D. M. (2007) *Chembiochem.* 8: 2039-2042; Kolpashchikov D. M. (2008). *J. Am. Chem. Soc.* 130: 2934-2935; Gerasimova et al., (2010) *Chembiochem* 11: 811-817) has been developed. In this approach two oligonucleotide probes form short hybrids with the analyte and generate a fluorescent signal upon tertiary complex formation. The approach enables SNP genotyping at room temperature with exceptional specificity.

SUMMARY

Briefly described, embodiments of this disclosure, among others, encompass systems, and their methods of use, for detecting a target analyte, wherein the system comprises: (a) a first oligonucleotide probe comprising: (i) at the 5'-terminus thereof, a reporter oligonucleotide-binding arm having a nucleotide sequence complementary to the nucleotide sequence of a first region of a reporter oligonucleotide; and (ii) at the 3'-terminus thereof, an analyte-binding arm having a nucleotide sequence characterized as selectively binding to a first region of a target analyte; (b) a second oligonucleotide probe comprising: (i) at the 3'-terminus thereof, a reporter oligonucleotide-binding arm having a nucleotide sequence complementary to the nucleotide sequence of a second region of a reporter oligonucleotide; and (ii) at the 5'-terminus thereof, an analyte-binding arm having a nucleotide sequence characterized as selectively binding to a second region of a target analyte; (c) a reporter oligonucleotide comprising: (i) a first region having a nucleotide sequence complementary to the reporter oligonucleotide-binding arm of the first oligonucleotide probe; (ii) a second region having a nucleotide sequence complementary to the reporter oligonucleotide-binding arm of the second oligonucleotide probe; (iii) a fluorophore and a quencher disposed on the reporter oligonucleotide whereby the fluorophore and quencher interact in the absence of a target analyte to quench fluorescence generated by the fluorophore; and (iv) a cleavable site disposed between the fluorescent label and the quencher, wherein the cleavable site is characterized as cleavable by a protein enzyme or a region of the first or the second oligonucleotide probe; and (d) an oligonucleotide-cleaving agent characterized as specifically cleaving the cleavable site of the reporter oligonucleotide.

In embodiments of this aspect of the system of the disclosure, the oligonucleotide-cleaving agent can be selected from the group consisting of an enzyme, a ribozyme, and a deoxyribozyme, and the ribozyme, and a deoxyribozyme can be optionally derived from a configuration of a region of the first oligonucleotide probe, the second oligonucleotide probe, or both the first and the second oligonucleotide probe.

In embodiments of this aspect of the system of the disclosure, the oligonucleotide-cleaving agent can be an enzyme selected from the group consisting of: a restriction endonuclease, an RNase H, a Flap-endonuclease-1 (FEN-1), and a DNA glycosylase. In embodiments of this aspect of the system of the disclosure, the reporter oligonucleotide-binding arm of at least one oligonucleotide probe can comprise a nucleotide sequence configured as a deoxyribozyme oligonucleotide-cleaving agent capable of specifically cleaving a site in the reporter oligonucleotide when the oligonucleotide probe is hybridized to the reporter oligonucleotide and to a target analyte.

At least one of the first oligonucleotide probe and the second oligonucleotide probe can further comprise a linker connecting the analyte-binding arm and the reporter oligonucleotide-binding arm of said oligonucleotide probe.

The reporter oligonucleotide can be a molecular beacon characterized as having a stem-loop configuration in the absence of a target analyte. In embodiments of this aspect of the system of the disclosure, at least one of the fluorophore and the quencher can be attached to the reporter oligonucleotide at the 5' or the 3' terminus thereof.

In embodiments of this aspect of the system of the disclosure, the system can further comprise a target analyte that with the first and second oligonucleotide probes, and the reporter oligonucleotide forms a quadripartite complex.

In embodiments of this aspect of the system of the disclosure, the nucleotide sequences of the analyte-binding arms of the first and the second oligonucleotide probes can be independently selected to specifically bind to a target analyte comprising a deoxyribonucleotide sequence, a ribonucleotide sequence, a double-stranded nucleic acid, a peptide, a polypeptide, or a variant thereof.

The system of the disclosure, the system can further comprise a plurality of oligonucleotide probe pairs, each probe pair comprising a first oligonucleotide probe and a second oligonucleotide probe. The plurality of oligonucleotide probe pairs can selectively bind to a plurality of sites of a single target analyte or to a plurality of target analytes.

In embodiments of this aspect of the system of the disclosure, the first or the second oligonucleotide probe can be tethered to a substrate and can be disposed on the substrate as an array.

Another aspect of the disclosure encompasses embodiments of method of identifying a target nucleotide sequence comprising the steps of: (i) obtaining a test sample; (ii) forming a reaction mix by combining the test sample with: (a) a first oligonucleotide probe comprising: (i) at the 5'-terminus thereof, a reporter oligonucleotide-binding arm having a nucleotide sequence complementary to the nucleotide sequence of a first region of a reporter oligonucleotide; and (ii) at the 3'-terminus thereof, an analyte-binding arm having a nucleotide sequence characterized as selectively binding to a first region of a target analyte; (b) a second oligonucleotide probe comprising: (i) at the 3'-terminus thereof, a reporter oligonucleotide-binding arm having a nucleotide sequence complementary to the nucleotide sequence of a second region of a reporter oligonucleotide; and (ii) at the 5'-terminus thereof, an analyte-binding arm having a nucleotide sequence characterized as selectively binding to a second region of a target analyte; (c) a reporter oligonucleotide comprising: (i) a first region having a nucleotide sequence complementary to the reporter oligonucleotide-binding arm of the first oligonucleotide probe; (ii) a second region having a nucleotide sequence complementary to the reporter oligonucleotide-binding arm of the second oligonucleotide probe; (iii) a fluorophore and a quencher disposed on the reporter oligonucleotide whereby said fluorophore and quencher interact in the absence of a target analyte to quench fluorescence generated by the fluorophore; and (iv) a cleavable site disposed between the fluorescent label and the quencher, wherein the cleavable site is characterized as cleavable by a protein enzyme or a region of the first or the second oligonucleotide probe, and (d) an oligonucleotide-cleaving agent characterized as specifically cleaving the cleavable site of the reporter oligonucleotide; under conditions suitable for the formation of a quadripartite complex between the analyte-binding arms of the first and the second oligonucleotide probes, a target analyte in the test sample, and the reporter oligonucleotide, thereby exposing a cleavable site of the reporter oligonucleotide for cleavage; (iii) allowing cleavage of a cleavable site of the reporter oligonucleotide, thereby releasing the fluorophore, the quencher, or both the fluorophore and the quencher, from the complex; (iv) illuminating the reaction mix at a wavelength suitable for inducing a fluorescent emission by the fluorophore; and (v) detecting the fluorescence emitted by the fluorophore, thereby detecting the presence of the target analyte in the sample.

Yet another aspect of the disclosure encompasses embodiments of a kit comprising: (a) a first oligonucleotide probe comprising: (i) at the 5'-terminus thereof, a reporter oligonucleotide-binding arm having a nucleotide sequence complementary to the nucleotide sequence of a first region of a reporter oligonucleotide; (ii) at the 3'-terminus thereof, an analyte-binding arm having a nucleotide sequence characterized as selectively binding to a first region of a target analyte; and (iii) optionally, a linker region covalently linking the reporter oligonucleotide-binding arm and the analyte-binding arm; (b) a second oligonucleotide probe comprising: (i) at the 3'-terminus thereof, a reporter oligonucleotide-binding arm having a nucleotide sequence complementary to the nucleotide sequence of a second region of a reporter oligonucleotide; (ii) at the 5'-terminus thereof, an analyte-binding arm having a nucleotide sequence characterized as selectively binding to a second region of a target analyte; and (iii) optionally, a linker region covalently linking the reporter oligonucleotide-binding arm and the analyte-binding arm; (c) a reporter oligonucleotide comprising: (i) a first region having a nucleotide sequence complementary to the reporter oligonucleotide-binding arm of the first oligonucleotide probe; (ii) a second region having a nucleotide sequence complementary to the reporter oligonucleotide-binding arm of the second oligonucleotide probe; (iii) a fluorophore and a quencher disposed on the reporter oligonucleotide whereby said fluorophore and quencher interact in the absence of a target analyte to quench fluorescence generated by the fluorophore; and (iv) a cleavable site disposed between the fluorescent label and the quencher, wherein the cleavable site is characterized as cleavable by a protein enzyme or a region of the first or the second oligonucleotide probe; or a plurality of oligonucleotide probe pairs, each probe pair comprising a first oligonucleotide probe and a second oligonucleotide probe, wherein the plurality of oligonucleotide probe pairs selectively binds to a plurality of sites of a single target analyte or to a plurality of target analytes, and wherein one oligonucleotide probe in each probe pair optionally is tethered to a substrate, and optionally disposed on the substrate as an array; (d) optionally, an oligonucleotide-cleaving agent characterized as specifically cleaving the cleavable site of the reporter oligonucleotide; and (e) packaging and instructions for the use of the kit to detect a target analyte in a test sample.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 6 is a scheme showing an RNase HU-based probe assay. A ribonucleotide inserted in the reporter oligonucleotide is indicated as rA.

FIG. 7 is a scheme showing an endonuclease-based assay.

FIG. 10 is a scheme showing microarrays of enzyme assisted probes.

FIG. 11 is a scheme showing a deoxyribozyme-assisted binary probe. One (strand β) or both reporter oligonucleotide-binding arms of the probe contain a deoxyribozyme sequence. The deoxyribozyme cleaves the reporter oligonucleotide substrate in the quadripartite complex (Panel B). X in the reporter oligonucleotide indicates the cleavage site.

Figure 1:
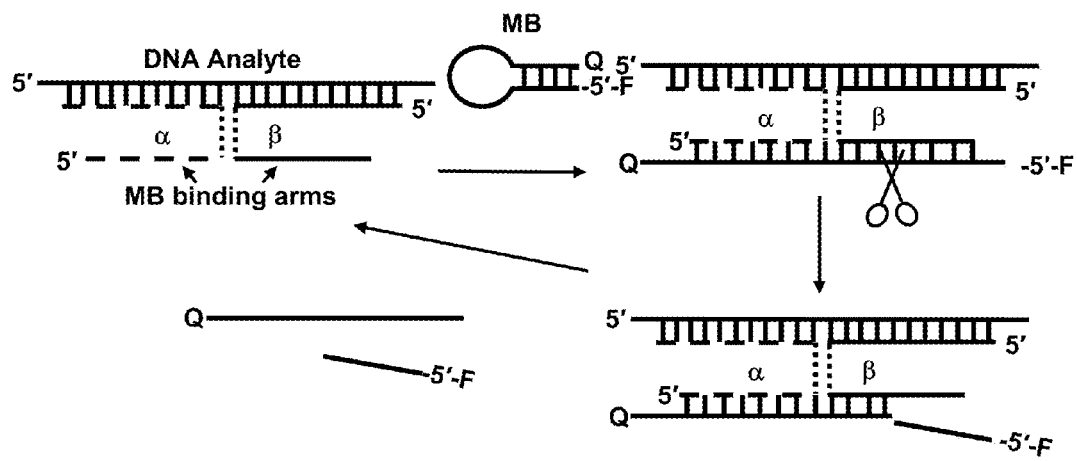
FIG. 1 is a scheme illustrating an embodiment of Enz-BDP1.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

In describing and claiming the disclosed subject matter, the following terminology will be used in accordance with the definitions set forth below.

The terms "oligonucleotide" and "polynucleotide" as used herein refer to any polyribonucleotide or polydeoxyribonucleotide that may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

The term "nucleotide" as used herein refers to a sub-unit of a nucleic acid (whether DNA or RNA or an analogue thereof) which may include, but is not limited to, a phosphate group, a sugar group and a nitrogen containing base, as well as analogs of such sub-units. Other groups (e.g., protecting groups) can be attached to the sugar group and nitrogen containing base group. It will be appreciated that, as used herein, the terms "nucleotide" and "nucleoside" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., diaminopurine and its deravitives, inosine and its deravitives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine, and 2,6-diaminopurine.

The term "hybridization" as used herein refers to the process of association of two nucleic acid strands to form an anti-parallel duplex stabilized by means of hydrogen bonding between residues of the opposite nucleic acid strands. The terms "hybridizing" and "binding", with respect to polynucleotides, are used interchangeably and is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions.

The terms "target" and "target analyte" as used herein refer to an oligonucleotide, peptide or polypeptide for which it is desired to detect. The target analyte for use in the methods herein disclosed may be an isolated oligonucleotide, peptide or polypeptide, an oligonucleotide, peptide or polypeptide immobilized on a solid support, or in free solution. Alternatively, the target oligonucleotide, peptide or polypeptide may be on a cell surface, the cell being isolated from a plant or animal host, a cultured cell or a cell or population of cells in a tissue of a plant or animal.

The term "complementary" as used herein refers to a sufficient number in the oligonucleotide of complementary base pairs in its sequence to interact specifically (hybridize) with the target nucleic acid sequence to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

By "immobilized on a solid support" is meant that an oligonucleotide is attached to a substance at a particular location in such a manner that the system containing the immobilized fragment, primer or oligonucleotide may be subjected to washing or other physical or chemical manipulation without being dislodged from that location. A number of solid supports and means of immobilizing nucleotide-containing molecules to them are known in the art; any of these supports and means may be used in the methods of this disclosure.

The terms "probe" and "oligonucleotide probe" as used herein refer to oligonucleotides nucleic acid sequences of variable length used in the detection of identical, similar, or complementary nucleic acid sequences by hybridization.

A "restriction enzyme" refers to an endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

The term "RNase HII" as used herein refers to Ribonuclease HII which is an endoribonuclease that preferentially nicks 5' to a ribonucleotide within the context of a DNA duplex. The enzyme leaves 5' phosphate and 3' hydroxyl ends. RNase HII will also nick at multiple sites along the RNA portion of an Okazaki fragment.

The term "reporter oligonucleotide" as used herein refers to an oligonucleotide having a fluorophore moiety and a quencher moiety attached thereto. The term "molecular beacon" and "oligonucleotide molecular beacon" as used herein refer to a form of a reporter oligonucleotide having a fluorophore- and quencher-labeled stem-loop structured oligodeoxyribonucleotide that is widely used for real-time detection of specific RNA/DNA sequences. In the stem-loop conformation, a fluorophore is brought close to the quencher enabling efficient fluorescent quenching. Hybridization to a complementary DNA/RNA target switches the molecular beacon conformation to elongated, which is accompanied by the fluorescence increase.

The term "fluorophore" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28. FW=792. Suitable fluorophores (chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.,), HILYTE® Fluors (AnaSpec), and DYLITE° Fluors (Pierce, Inc).

The term "aptamer" as used herein is an isolated nucleic acid molecule that binds with high specificity and affinity to a target, such as a protein. An aptamer is a three dimensional structure held in certain conformation(s) that provides chemical contacts to specifically bind its given target. Although aptamers are nucleic acid based molecules, there is a fundamental difference between aptamers and other nucleic acid molecules such as genes and mRNA. In the latter, the nucleic acid structure encodes information through its linear base sequence and thus this sequence is of importance to the function of information storage. In complete contrast, aptamer function, which is based upon the specific binding of a target molecule, is not entirely dependent on a conserved linear base sequence (a non-coding sequence), but rather a particular secondary/tertiary/quaternary structure. Any coding potential that an aptamer may possess is entirely fortuitous and plays no role whatsoever in the binding of an aptamer to its cognate target.

The terms "fluorescence quencher" or "quencher" as used herein refer to a molecule that interferes with the fluorescence emitted by a fluorophore. This quencher can be selected from non-fluorescent aromatic molecules, to avoid parasitic emissions. Exemplary quenchers include, but are not limited to, such as a Dabsyl or a BLACK HOLE QUENCHER® that are nonfluorescent aromatic molecules that prevent the emission of fluorescence when they are physically near a fluorophore. The quencher can also be, but is not limited to, a fluorescent molecule, for example TAMRA (carboxytetramethylrhodamine). When the quencher is a fluorescent dye, its fluorescence wavelength is typically substantially different from that of the reporter dye and the quencher fluorescence is usually not monitored during an assay.

The terms "quench" or "quenches" or "quenching" or "quenched" as used herein refer to reducing the signal produced by a molecule. It includes, but is not limited to, reducing the signal produced to zero or to below a detectable limit. Hence, a given molecule can be "quenched" by, for example, another molecule and still produce a detectable signal albeit the size of the signal produced by the quenched molecule will be smaller when the molecule is quenched than when the molecule is not quenched.

The term "solid support" is used herein refers to any insoluble and inert inorganic or organic material, preferably having a large surface area to which surface organic molecules can be attached through bond formation or absorbed through electronic or static interactions. Representative examples of a "solid support" in context with the present invention are silicates, such as $SiO_2$ resin, including, but not limited to, ion-exchange resins, glass, dextranes, celluloses or hydrophilic or hydrophobic polymers.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

DESCRIPTION

Generally, the assay system of the disclosure is composed of two short synthetic oligonucleotide probes (stands α and β as shown, for example, in FIG. 1), a reporter oligonucleotide labeled with both a fluorophore- and quencher (FIG. 1), and a DNA processing enzyme, or a nucleic acid processing activity catalyzed by a region of at least one of the two oligonucleotide probes. Both strands α and β contain at least one nucleotide sequence region complementary to a region or regions of the reporter oligonucleotide (reporter binding arms), and at least one nucleotide sequence region complementary to at least one region of the analyte (analyte binding arms). In the presence of a target analyte such as, but not limited to, a nucleic acid, strands α and β, the reporter oligonucleotide, and the analyte form a quadripartite complex. This complex can be specifically recognized by a DNA processing enzyme, a ribozyme, or deoxyribozyme (generated by the nucleotide sequence and the conformation thereof of at least one of the oligonucleotide probes) and which recognizes a specific site in the reporter oligonucleotide and catalyzes a reaction cleaving the oligonucleotide and separation of two different molecules, each bearing the fluorophore or the quencher, but not both, as (FIG. 1, right). The resultant increase in fluorescence can be quantitatively detected by a conventional fluorimeter.

High specificity for a target analyte of the probe can be predetermined by independent or semi-independent hybridization of the analyte-binding arms of stands α and β to the analyte. Each arm can form a short hybrid with the analyte that is sensitive to a minor variation such as single base mispairing.

It is contemplated that in certain embodiments, a single analyte molecule such as an oligonucleotide can accommodate several quadripartite complexes, each of which can be processed by enzyme cleavage to resulting in a fluorophore and/or quencher release, thereby increasing sensitivity of the assay, or able to detect a plurality of nucleotide sequence variations within the single analyte molecule.

The reporter oligonucleotide does not interact directly with the analyte and is, therefore, independent of the analyte sequence. Accordingly, it is possible to optimize the reporter oligonucleotide for use as a universal reporter not limited by the nature of the target analyte. The reporter oligonucleotide can be costly to synthesize due to the attachment reactions to link a fluorophore and the quencher to the beacon. A universal reporter can substantially reduce the cost of the multiplex assay systems of the disclosure. Embodiments of the systems of the present disclosure are shown in Examples 1-9 below. The desired oligonucleotide probes can be defined, synthesized, and purified my methods well known in the art. Attachment of both a fluorophore and a fluorescence quencher to the universal reporter oligonucleotide are also well known in the art.

Embodiments of the present disclosure, therefore, encompass a PCR-free assay system that allows fluorescent detection of specific target analytes, including, but not limited to, specific nucleotide sequences, with high selectivity and sensitivity. The advantages of the assay over currently available approaches include, but are not limited to, discrimination of signal nucleotide substitution in an analyzed nucleic acid with accuracy even at ambient temperatures, reduced detection limits comparable to enzymatic amplification, and lower costs per assay since only two short unmodified oligonucleotides are synthesized for each new analyte sequence, while all other reagents are analyte independent and, therefore, can be obtained in bulk amount and utilized efficiently. In particular, the systems of the present disclosure provide an amplification of the detected fluorescent signal by allowing repeated formation of quencher-dissociated fluorophores.

The systems of the present disclosure, accordingly, comprise two oligonucleotide probes, each probe comprising an analyte-binding arm, the nucleotide sequence of which may be selected to specifically bind to a target analyte, and a reporter oligonucleotide-binding arm, the sequence of which may specifically bind to a region within the nucleotide sequence of a reporter oligonucleotide. The systems of the present disclosure further comprise a reporter oligonucleotide having regions of nucleotide sequence complementary to the sequences of the reporter oligonucleotide-binding arm of the oligonucleotide probes. The target analyte nucleotide sequences (or regions of a peptide or polypeptide target analyte) selected for binding to the analyte-binding arms of the two oligonucleotide probes are chosen so as to place the two probe molecules in sufficiently close to one another to allow an interaction between the reporter-binding arms of both of the probes and the complementary regions of the reporter oligonucleotide itself (and thereby generating a "binary probe").

The reporter oligonucleotides of the disclosure also include a fluorophore and a quencher moiety that may be located at the extreme ends of the reporter oligonucleotide molecule, or internally but separated such that if the reporter oligonucleotide is elongated there is no interaction between the fluorophore and the quencher.

In the embodiments of the present disclosure, the reporter oligonucleotides further include at least one cleavable site that may be specifically cleaved by a protein enzyme, or by a ribozyme or a deoxyribozyme that is formed by the three-dimensional configuration of the nucleotide sequence of one of the two oligonucleotide probes. While it is contemplated that each of the oligonucleotide probes can independently form a ribozyme or a deoxyribozyme from the configuration of the reporter oligonucleotide-binding arms, it is not within the scope of the embodiments of the present disclosure for the ribozyme or deoxyribozyme to result from interaction of the two probes with each other.

In the systems as encompassed by the present disclosure, two oligonucleotide probes that can be made of DNA or RNA, or a combination of both. Each strand of the DNA or RNA probe has a customized fragment that has sequence complementarity to a selected target analyte (the analyte-binding arm), and a region having sequence complementarity to a region of a reporter oligonucleotide such as, but not limited to, a molecular beacon. The analyte-binding and reporter-binding arms optionally may be connected to each other by a linker. It is further contemplated that the oligonucleotide probes can have additional nucleotide sequences added to one or both of the free ends of each strand of the probe and which are complementary to, and can hybridize with, a region of the respective strand to form a stem-loop structure. These additional stem-loop-forming sequences are termed structure stabilization arms (SSA) (see below).

In the embodiments of the disclosure, it is contemplated that the two oligonucleotide probes may hybridize through their respective analyte-binding arms with a target analyte. While the targeted analyte can be advantageously a nucleic acid sequence, it is considered within the scope of the disclosure for the analyte to be any biomolecule that may specifically bind to the analyte-binding arms of a pair of oligonucleotide probes, including, but not limited to, a peptide, a polypeptide, the glycosylated variants thereof, and the like, wherein the analyte-binding arms may be an aptamer. Analytes may be a component of, or isolated from a biological source, including, but not limited to, a eukaryotic cell or tissue, a prokaryotic organism such as a bacterium or virus, or any other analyte to which the sequences of the pair of oligonucleotides may specifically bind. Nucleic acid target analytes can be, but are not limited to, a DNA strand, an RNA strand, a nucleic acid double helix, and the like.

The reporter oligonucleotide of the systems of the disclosure comprises two nucleic acid sequences that can hybridize to the reporter oligonucleotide-binding arms of a pair of oligonucleotide probes. Attached to the reporter oligonucleotide are a fluorophore and a quencher. In the absence of binding to the oligonucleotide probes, the reporter oligonucleotide preferentially assumes a configuration, such as a stem-loop structure, where the fluorophore and the quencher are brought into close proximity, whereupon the quencher suppresses fluorescence emission by the fluorophore if irradiated by incident excitor light.

In the systems provided by the disclosure, the reporter oligonucleotide may be, but is not limited to, a deoxyribonucleic acid that may have a stem-loop conformation forming a molecular beacon. Although most molecular beacons are DNA oligonucleotides, there is no technical obstacle to making molecular beacons that are RNA or chimeras of DNA and RNA for use in the new binary RNA oligonucleotide probes.

In some embodiments, the reporter may include one or more ribonucleotides that provide cleavable sites within the reporter nucleotide sequence. However, it is contemplated that the reporter oligonucleotide may comprise a nucleotide sequence that, when hybridized with a complementary sequence in the reporter-binding-arm of an oligonucleotide probe, forms a site that can be recognized and specifically cleaved by an enzyme.

The probe can be customized for any fluorophore including, but not limited to, FAM, TAMRA, Dy 750, HEX™, JOE, TET™, Texas Red-X, Alexa Fluor Dyes, Bodipy Dyes, CY Dyes, Rhodanine, dyes, WellRED Dyes, MAX, and TEX 613; and for any quencher including, but not limited to, black hole quenchers, Iowa Black Quenchers, and DABCYL. It is within the scope of the disclosure, however, for a plurality of systems to be combined, wherein a different target analyte is detectable by each system and each system incorporates a different and distinguishable fluorophore for the simultaneous detection of multiple analytes in a single test sample. Reporter oligonucleotide-binding arms on each strand are typically 3-20 nucleotides long, but routine experimentation based on the reporter oligonucleotide will determine the optimum length.

For example, and not intended to be limiting, at least one nucleotide sequence, when hybridized with a complementary sequence in the reporter-binding-arm of an oligonucleotide probe, forms a site that can be recognized and specifically cleaved by a restriction endonuclease. In another embodiment, the nucleotide sequence, when hybridized with a complementary sequence in the reporter-binding-arm of an oligonucleotide probe, can form a site that includes a ribonucleotide and which can be specifically cleaved by RNase HII. In all embodiments of the systems of the present disclosure, however, it is contemplated that the reporter oligonucleotide will have at least one cleavable site located between the fluorophore and the quencher.

In the assays using the systems and methods of the present disclosure, a test sample suspected of having a target analyte is contacted with a pair of oligonucleotide probes having analyte-binding arms that can specifically bind to the target analyte, and which may then bind to the analyte under the appropriate conditions. The reporter oligonucleotide-binding arms of the bound oligonucleotide probes can then preferentially bind to the corresponding complementary regions within the reporter oligonucleotide to form a quaternary, or quadripartite, complex such as illustrated in FIGS. 1, 3, 6-11. Initially, complexing of the reporter oligonucleotide with the oligonucleotide probes will elongate the reporter oligonucleotide, thereby dissociating the fluorophore and the quencher from each other and allowing, with a suitable wavelength of incident light, to generate a first level of fluorescence emission intensity. However, by then providing the system with a protein enzyme that specifically binds to, and cleaves, the cleavable site(s) of the reporter oligonucleotide, a fragment(s) of the reporter oligonucleotide bearing the fluorophore (or quencher, or both the fluorophore and the quencher) is released from the quadripartite complex, which then dissociates to reform with a new and uncleaved reporter oligonucleotide molecule to renew the cycle. Accordingly, the detectable fluorescence intensity becomes amplified, providing increased sensitivity of the assay to the target analyte.

In one embodiment of the assay system of the disclosure, however, the protein enzyme that can be used to specifically cleave the reporter oligonucleotide can be replaced by at least one of the reporter oligonucleotide-binding arms of the quadripartite complex assuming a configuration of a ribozyme (if the oligonucleotide-binding arm is an RNA sequence) or a deoxyribozyme (if the oligonucleotide-binding arm is an RNA sequence) that can specifically cleave a site within the reporter oligonucleotide sequence that includes a ribonucleotide, as illustrated in FIG. 11, for example.

For optimum selectivity, for example of SNPs, the analyte-binding arm of each strand of the probe ranges from about 6 to about 20 nucleotides in length, which makes the total analyte fragment region recognizable by a pair of oligonucleotide probes about 12 to about 40 nucleotides long. The analyte itself can be of any length from 12-40, to many thousand nucleotides. Analyte-binding arms of about 10 nucleotides are advantageous because a combined length of about 20 nucleotides of a target analyte will cover most unique sequences in the genome. Analyte-binding arms that recognize an analyte region with a combined length longer than about 20 nucleotides may have increased sensitivity.

Linkers

The analyte-binding- and reporter oligonucleotide-binding arms of an oligonucleotide probe of the systems of the present disclosure may be, but not necessarily, separated by a linker. For example, but not intended to be limiting, such a linker may be a stretch of nucleotides. Such a linker may, when the oligonucleotide probes are bound to a target analyte, hybridize to the linker of the second of the two probes bound to a target analyte, whereupon the two linkers may hybridize to form a double helix. However, it is also possible for the linker to be merely one or two nucleotides that cannot form a duplex double-helix, nor bind to the target analyte. It is further contemplated that the linker of an oligonucleotide probe may be, but not limited to, a flexible triethylene glycol linker.

Also within the scope of the disclosure are systems where one of the analyte-detecting oligonucleotide probes of a pair of such probes is immobilized to a solid substrate. The present disclosure therefore encompasses probes according to the present disclosure that are immobilized on a solid or flexible support, such as paper, nylon or other type of membrane, filter, chip, glass slide, microchips, microbeads, or any other such matrix, all of which are within the scope of this disclosure. The probe of this form is now called a "DNA chip". These DNA chips can be used for analyzing the SNPs of the present disclosure. The present disclosure further encompasses arrays or microarrays of nucleic acid molecules that are based on one or more of the sequences described herein. As used herein "arrays" or "microarrays" refers to an array of distinct polynucleotides or oligonucleotides synthesized on a solid or flexible support, such as paper, nylon or other type of membrane, filter, chip, glass slide, or any other suitable solid support. In one embodiment, the microarray is prepared and used according to the methods and devices described in U.S. Pat. Nos. 5,446,603; 5,545,531; 5,807,522; 5,837,832; 5,874,219; 6,114,122; 6,238,910; 6,365,418; 6,410,229; 6,420,114; 6,432,696; 6,475,808 and 6,489,159 and PCT Publication No. WO 01/45843 A2, the disclosures of which are incorporated by reference in their entireties.

Compositions and kits for the detection of analytes: The oligonucleotide primers and probes of the present disclosure have commercial applications in diagnostic kits for the detection of such as SNPs in biological specimens. A kit according to the disclosure may comprise any of the oligonucleotide primers or probes according to the disclosure and preferable includes packaging and instructions for the use thereof. An SNP detection kit may also include a lysing buffer for lysing cells contained in the specimen.

One aspect of the disclosure, therefore, encompasses embodiments of a system for detecting a target analyte, the system comprising: (a) a first oligonucleotide probe comprising: (i) at the 5'-terminus thereof, a reporter oligonucleotide-binding arm having a nucleotide sequence complementary to the nucleotide sequence of a first region of a reporter oligonucleotide; and (ii) at the 3'-terminus thereof, an analyte-binding arm having a nucleotide sequence characterized as selectively binding to a first region of a target analyte; (b) a second oligonucleotide probe comprising: (i) at the 3'-terminus thereof, a reporter oligonucleotide-binding arm having a nucleotide sequence complementary to the nucleotide sequence of a second region of a reporter oligonucleotide; and (ii) at the 5'-terminus thereof, an analyte-binding arm having a nucleotide sequence characterized as selectively binding to a second region of a target analyte; (c) a reporter oligonucleotide comprising: (i) a first region having a nucleotide sequence complementary to the reporter oligonucleotide-binding arm of the first oligonucleotide probe; (ii) a second region having a nucleotide sequence complementary to the reporter oligonucleotide-binding arm of the second oligonucleotide probe; (iii) a fluorophore and a quencher disposed on the reporter oligonucleotide whereby the fluorophore and quencher interact in the absence of a target analyte to quench fluorescence generated by the fluorophore; and (iv) a cleavable site disposed between the fluorescent label and the quencher, wherein the cleavable site is characterized as cleavable by a protein enzyme or a region of the first or the second oligonucleotide probe; and (d) an oligonucleotide-cleaving agent characterized as specifically cleaving the cleavable site of the reporter oligonucleotide.

In embodiments of this aspect of the system of the disclosure, the oligonucleotide-cleaving agent can be selected from the group consisting of an enzyme, a ribozyme, and a deoxyribozyme, and the ribozyme, and a deoxyribozyme can be optionally derived from a configuration of a region of the first oligonucleotide probe, the second oligonucleotide probe, or both the first and the second oligonucleotide probe.

In embodiments of this aspect of the system of the disclosure, the cleavable site of the reporter oligonucleotide can comprise a ribonucleotide.

In embodiments of this aspect of the system of the disclosure, the reporter oligonucleotide-binding arm of at least one oligonucleotide probe can comprise a nucleotide sequence that provides a site in the reporter oligonucleotide specifically cleavable by a restriction endonuclease when said oligonucleotide probe is hybridized to the reporter oligonucleotide, and the oligonucleotide-cleaving agent is said restriction endonuclease.

In embodiments of this aspect of the system of the disclosure, the oligonucleotide-cleaving agent can be an enzyme selected from the group consisting of: a restriction endonuclease, an RNase H, a Flap-endonuclease-1 (FEN-1), and a DNA glycosylase.

In embodiments of this aspect of the system of the disclosure, the reporter oligonucleotide-binding arm of at least one oligonucleotide probe can comprise a nucleotide sequence configured as a deoxyribozyme oligonucleotide-cleaving agent capable of specifically cleaving a site in the reporter oligonucleotide when the oligonucleotide probe is hybridized to the reporter oligonucleotide and to a target analyte.

In embodiments of this aspect of the system of the disclosure, the at least one of the first oligonucleotide probe and the second oligonucleotide probe can further comprise a linker connecting the analyte-binding arm and the reporter oligonucleotide-binding arm of said oligonucleotide probe.

In embodiments of this aspect of the system of the disclosure, the reporter oligonucleotide can be a molecular beacon characterized as having a stem-loop configuration in the absence of a target analyte.

In embodiments of this aspect of the system of the disclosure, at least one of the fluorophore and the quencher can be attached to the reporter oligonucleotide at the 5' or the 3' terminus thereof.

In embodiments of this aspect of the system of the disclosure, the system can further comprise a target analyte and wherein the analyte, the first and second oligonucleotide probes, and the reporter oligonucleotide form a quadripartite complex, thereby providing a configuration of the cleavable site of the reporter oligonucleotide allowing said site to be cleaved.

In embodiments of this aspect of the system of the disclosure, the nucleotide sequences of the analyte-binding arms of the first and the second oligonucleotide probes can be independently selected to specifically bind to a target analyte comprising a deoxyribonucleotide sequence, a ribonucleotide sequence, a double-stranded nucleic acid, a peptide, a polypeptide, or a variant thereof.

In embodiments of this aspect of the system of the disclosure, the first or the second oligonucleotide probe can be tethered to a substrate.

In embodiments of this aspect of the system of the disclosure, the system can further comprise a plurality of oligonucleotide probe pairs, each probe pair comprising a first oligonucleotide probe and a second oligonucleotide probe.

In embodiments of this aspect of the system of the disclosure, the plurality of oligonucleotide probe pairs can selectively bind to a plurality of sites of a single target analyte.

In embodiments of this aspect of the system of the disclosure, the plurality of oligonucleotide probe pairs can selectively bind to a plurality of target analytes.

In embodiments of this aspect of the system of the disclosure, one oligonucleotide probe in each probe pair can be tethered to a substrate.

In embodiments of this aspect of the system of the disclosure, the oligonucleotide probe in each probe pair tethered to a substrate can be disposed on the substrate as an array.

Another aspect of the disclosure encompasses embodiments of method of identifying a target nucleotide sequence comprising the steps of: (i) obtaining a test sample; (ii) forming a reaction mix by combining the test sample with: (a) a first oligonucleotide probe comprising: (i) at the 5'-terminus thereof, a reporter oligonucleotide-binding arm having a nucleotide sequence complementary to the nucleotide sequence of a first region of a reporter oligonucleotide; and (ii) at the 3'-terminus thereof, an analyte-binding arm having a nucleotide sequence characterized as selectively binding to a first region of a target analyte; (b) a second oligonucleotide probe comprising: (i) at the 3'-terminus thereof, a reporter oligonucleotide-binding arm having a nucleotide sequence complementary to the nucleotide sequence of a second region of a reporter oligonucleotide; and (ii) at the 5'-terminus thereof, an analyte-binding arm having a nucleotide sequence characterized as selectively binding to a second region of a target analyte; (c) a reporter oligonucleotide comprising: (i) a first region having a nucleotide sequence complementary to the reporter oligonucleotide-binding arm of the first oligonucleotide probe; (ii) a second region having a nucleotide sequence complementary to the reporter oligonucleotide-binding arm of the second oligonucleotide probe; (iii) a fluorophore and a quencher disposed on the reporter oligonucleotide whereby said fluorophore and quencher interact in the absence of a target analyte to quench fluorescence generated by the fluorophore; and (iv) a cleavable site disposed between the fluorescent label and the quencher, wherein the cleavable site is characterized as cleavable by a protein enzyme or a region of the first or the second oligonucleotide probe, and (d) an oligonucleotide-cleaving agent characterized as specifically cleaving the cleavable site of the reporter oligonucleotide; under conditions suitable for the formation of a quadripartite complex between the analyte-binding arms of the first and the second oligonucleotide probes, a target analyte in the test sample, and the reporter oligonucleotide, thereby exposing a cleavable site of the reporter oligonucleotide for cleavage; (iii) allowing cleavage of a cleavable site of the reporter oligonucleotide, thereby releasing the fluorophore, the quencher, or both the fluorophore and the quencher, from the quadripartite complex; (iv) illuminating the reaction mix at a wavelength suitable for inducing a fluorescent emission by the fluorophore; and (v) detecting the fluorescence emitted by the fluorophore, thereby detecting the presence of the target analyte in the sample.

In embodiments of this aspect of the system of the disclosure, the oligonucleotide-cleaving agent can be selected from the group consisting of an enzyme, a ribozyme, and a deoxyribozyme, and the ribozyme, and a deoxyribozyme can be optionally derived from a configuration of a region of the first oligonucleotide probe, the second oligonucleotide probe, or both the first and the second oligonucleotide probe.

In embodiments of this aspect of the system of the disclosure, the cleavable site of the reporter oligonucleotide can comprise a ribonucleotide.

In embodiments of this aspect of the system of the disclosure, the reporter oligonucleotide-binding arm of at least one oligonucleotide probe can comprise a nucleotide sequence that provides a site in the reporter oligonucleotide specifically cleavable by a restriction endonuclease when said oligonucleotide probe is hybridized to the reporter oligonucleotide.

In embodiments of this aspect of the system of the disclosure, the cleavable site of the reporter oligonucleotide when in the presence of a target analyte can be cleavable by an enzyme selected from the group consisting of: a restriction endonuclease, an RNase H, a Flap-endonuclease-1 (FEN-1), and a DNA glycosylase.

In embodiments of this aspect of the system of the disclosure, the reporter oligonucleotide-binding arm of at least one oligonucleotide probe can comprise a nucleotide sequence configured as a deoxyribozyme capable of specifically cleaving a site in the reporter oligonucleotide when the oligonucleotide probe is hybridized to the reporter oligonucleotide and to a target analyte.

In embodiments of this aspect of the system of the disclosure, the first oligonucleotide probe and the second oligonucleotide probe the analyte-binding arm and the reporter oligonucleotide-binding arm thereof can be connected by a linker.

In embodiments of this aspect of the system of the disclosure, the reporter oligonucleotide can be a molecular beacon and can be characterized as having a stem-loop configuration in the absence of a target analyte.

In embodiments of this aspect of the system of the disclosure, the at least one of the fluorophore and the quencher can be attached to the reporter oligonucleotide at the 5' or the 3' terminus thereof.

In embodiments of this aspect of the system of the disclosure, the method can further comprise a target analyte wherein the analyte, the first and second oligonucleotide probes, and the reporter oligonucleotide can form a quadripartite complex, thereby providing a configuration of the cleavable site of the reporter oligonucleotide allowing said site to be cleaved.

In embodiments of this aspect of the system of the disclosure, the nucleotide sequences of the analyte-binding arms of the first and the second oligonucleotide probes can be independently selected to specifically bind to a target analyte comprising a deoxyribonucleotide sequence, a ribonucleotide sequence, a double-stranded nucleic acid, a peptide, a polypeptide, or a variant thereof.

In embodiments of this aspect of the system of the disclosure, the first or the second oligonucleotide probe can be tethered to a substrate.

In embodiments of this aspect of the system of the disclosure, the method can comprise a plurality of oligonucleotide probe pairs, each probe pair comprising a first oligonucleotide probe and a second oligonucleotide probe.

In embodiments of this aspect of the system of the disclosure, the plurality of oligonucleotide probe pairs can selectively bind to a plurality of sites of a single target analyte.

In embodiments of this aspect of the system of the disclosure, the plurality of oligonucleotide probe pairs can selectively bind to a plurality of target analytes.

In embodiments of this aspect of the system of the disclosure, one oligonucleotide probe in each probe pair can be tethered to a substrate.

In embodiments of this aspect of the system of the disclosure, the oligonucleotide probe in each probe pair tethered to a substrate can be disposed on the substrate as an array.

Yet another aspect of the disclosure encompasses embodiments of a kit comprising: (a) a first oligonucleotide probe comprising: (i) at the 5'-terminus thereof, a reporter oligonucleotide-binding arm having a nucleotide sequence complementary to the nucleotide sequence of a first region of a reporter oligonucleotide; (ii) at the 3'-terminus thereof, an analyte-binding arm having a nucleotide sequence characterized as selectively binding to a first region of a target analyte; and (iii) optionally, a linker region covalently linking the reporter oligonucleotide-binding arm and the analyte-binding arm; (b) a second oligonucleotide probe comprising: (i) at the 3'-terminus thereof, a reporter oligonucleotide-binding arm having a nucleotide sequence complementary to the nucleotide sequence of a second region of a reporter oligonucleotide; (ii) at the 5'-terminus thereof, an analyte-binding arm having a nucleotide sequence characterized as selectively binding to a second region of a target analyte; and (iii) optionally, a linker region covalently linking the reporter oligonucleotide-binding arm and the analyte-binding arm; (c) a reporter oligonucleotide comprising: (i) a first region having a nucleotide sequence complementary to the reporter oligonucleotide-binding arm of the first oligonucleotide probe; (ii) a second region having a nucleotide sequence complementary to the reporter oligonucleotide-binding arm of the second oligonucleotide probe; (iii) a fluorophore and a quencher disposed on the reporter oligonucleotide whereby said fluorophore and quencher interact in the absence of a target analyte to quench fluorescence generated by the fluorophore; and (iv) a cleavable site disposed between the fluorescent label and the quencher, wherein the cleavable site is characterized as cleavable by a protein enzyme or a region of the first or the second oligonucleotide probe; or a plurality of oligonucleotide probe pairs, each probe pair comprising a first oligonucleotide probe and a second oligonucleotide probe, wherein the plurality of oligonucleotide probe pairs selectively binds to a plurality of sites of a single target analyte or to a plurality of target analytes, and wherein one oligonucleotide probe in each probe pair optionally is tethered to a substrate, and optionally disposed on the substrate as an array; (d) optionally, an oligonucleotide-cleaving agent characterized as specifically cleaving the cleavable site of the reporter oligonucleotide; and (e) packaging and instructions for the use of the kit to detect a target analyte in a test sample.

In embodiments of this aspect of the system of the disclosure, the oligonucleotide-cleaving agent can be selected from the group consisting of an enzyme, a ribozyme, and a deoxyribozyme, and the ribozyme, and a deoxyribozyme are optionally derived from a configuration of a region of the first oligonucleotide probe, the second oligonucleotide probe, or both the first and the second oligonucleotide probe.

In embodiments of this aspect of the system of the disclosure, the reporter oligonucleotide-binding arm of at least one oligonucleotide probe can comprise a nucleotide sequence configured as a deoxyribozyme capable of specifically cleaving a site in the reporter oligonucleotide when the oligonucleotide probe is hybridized to the reporter oligonucleotide and to a target analyte.

In embodiments of this aspect of the system of the disclosure, the reporter oligonucleotide can be a molecular beacon and is characterized as having a stem-loop configuration in the absence of a target analyte.

In embodiments of this aspect of the system of the disclosure, the oligonucleotide probe can be tethered to a substrate.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

One embodiment of the system of the present disclosure provides a molecular beacon (molecular beacon), which acts as a reporter, and two DNA strands: strand α and strand β. Each of the strands contains a fragment complementary to molecular beacon (molecular beacon-binding arm) and a fragment complementary to a DNA analyte. In the presence of the analyte, the probe forms a quadripartite complex, in which BDP strands serve as adaptors to connect the analyte and the molecular beacon reporter. The molecular beacon-binding arm of BDP strand β is complementary to the molecular beacon fragment, which contains a single ribonucleotide embedded into DNA sequence. RNase HII recognizes the ribonucleotide-containing duplex fragment and cleaves the phosphodiester bond at the 5'-end of the ribonucleotide. As a result, the molecular beacon is hydrolyzed into two fragments, which dissociate from the quadripartite complex. The resulting tripartite complex of the analyte with two strands of Enz-BDP1 can bind another molecule of molecular beacon from solution to form the complex, which is then recognized by the enzyme. Therefore, the signal amplification is achieved.

TABLE 1

The sequences of analyte HepC30 and oligonucleotides constituting Enz-BDP1

| | |
|---|---|
| HepC30 | 5'-TGCCCCGGAGGTCTGTAGACCGTGCACC-3' (SEQ ID NO.: 1) |
| Enz-BDP1 strand α | 5'-GACCATCTCAGACCTCCCGGG-3' (SEQ ID NO.: 2) |
| Enz-BDP1 strand β | 5'-CACGGTCTACGTTCCTATAG-3' (SEQ ID NO.: 3) |
| Molecular Beacon 1 (MB1) | 5'-F-CCGACTCACTATaGGAAGAGATGGTCGG-Q-3' (SEQ ID NO.: 4)[a] |

[a]Small case indicates ribonucleotide

F and Q designate the Fluorescein and Black Hole 1 quencher, respectively.

Example 2

Figure 2:
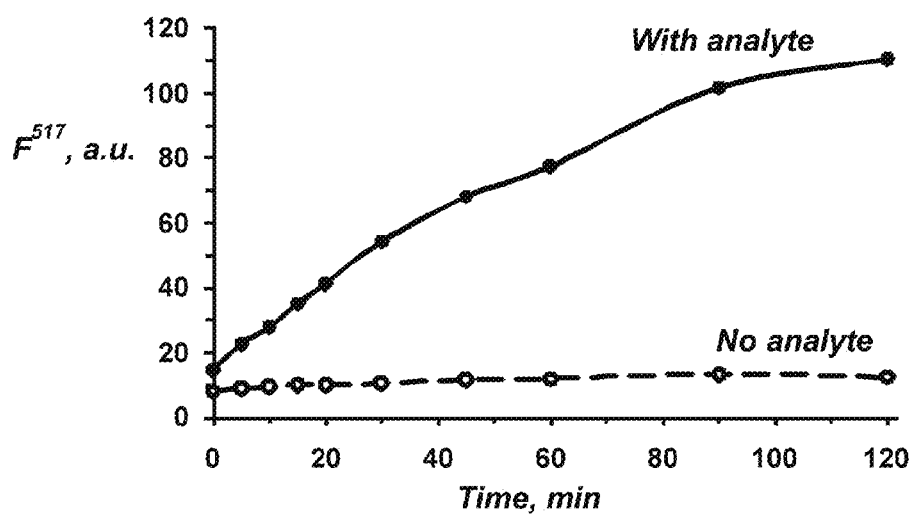
FIG. 2 is a graph showing the fluorescence enhancement of Enz-BDP1 together with RNase HII in the presence (●) or in the absence (○) of the analyte HepC30 (SEQ ID NO.: 1).

Referring now to FIG. 2, another embodiment of the disclosure provides fluorescence enhancement of Enz-BDP1 together with RNase HII in the presence or in the absence of the analyte HepC30. Reaction conditions: 10 nM molecular beacon 1, 100 nM strands α and β, 10 nM HepC30; 2U RNase HII; 20 mM Tris-HCl, pH 8.8; 10 mM $(NH_4)_2SO_4$, 10 mM KCl, 25 mM MgCl, 0.1% Triton X-100; 30° C.

Example 3

Figure 3:
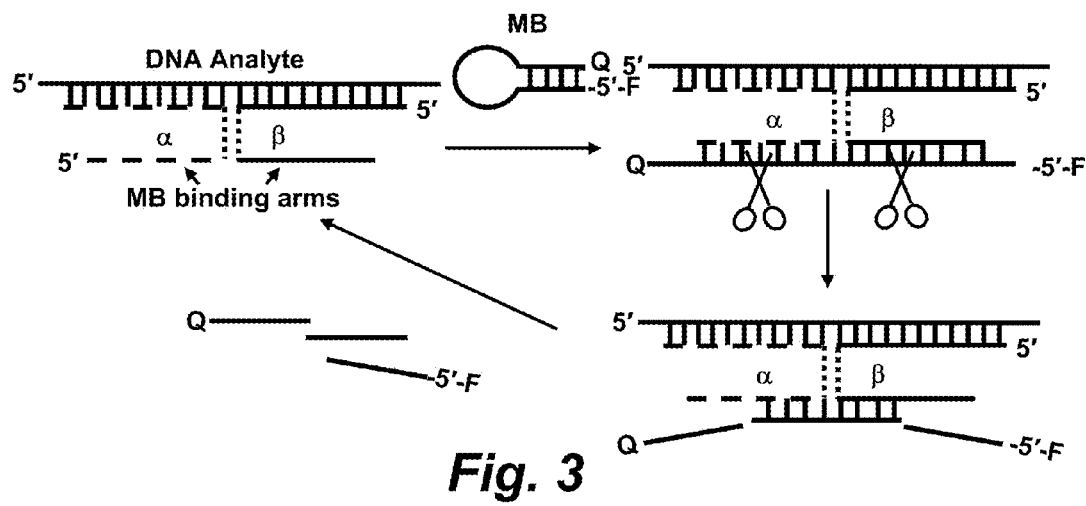
FIG. 3 is a scheme illustrating an embodiment of Enz-BDP2.

Referring now to FIG. 3, another embodiment of the disclosure provides a design of Enz-BDP2. The probe consists of a reporter oligonucleotide (in this example, but not limited thereto, a molecular beacon) and two DNA strands: strand α and strand β. Each of the strands contains a fragment complementary to the reporter oligonucleotide (reporter oligonucleotide-binding arm) and a fragment complementary to a DNA analyte. In the presence of the analyte, the probe forms a quadripartite complex, in which BDP strands serve as adaptors to connect the analyte and the reporter oligonucleotide. Reporter oligonucleotide-binding arms of the BDP strands are complementary to two reporter oligonucleotide fragments, each of which contains a single ribonucleotide embedded into DNA sequence. RNase HII recognizes the duplex fragments and cleaves the phosphodiester bond at the 5' end of the ribonucleotide. As a result, reporter oligonucleotide is hydrolyzed into three fragments—the fluorophore-containing fragment, the middle fragment, and the quencher-containing fragment, which dissociate from the quadripartite complex. The resulting tripartite complex of the analyte with two strands of Enz-BDP2 can bind another molecule of the reporter oligonucleotide from solution to form the complex, which is then recognized by the enzyme. Therefore, the signal amplification is achieved.

TABLE 2

The sequences of analyte HepC40 and oligonucleotides constituting Enz-BDP2

| | |
|---|---|
| HepC40 | TTCATCGTCTCGCCGCAGTACCACTGGTTTGTGCAAGAAT (SEQ ID NO.: 5) |
| Enz-BDP2 strand α | GATCTATTGGTACTGCGGCGA (SEQ ID NO.: 6) |
| Enz-BDP2 strand β | GCACAAACCAGTGTATGTTAAC (SEQ ID NO.: 7) |
| Molecular Beacon 2 (MB2) | FAM-5'-CGCGTTAaCATACAATaGATCGCG-BHQ1 (SEQ ID NO.: 8)[a] |

[a]Small case indicates ribonucleotide

Figure 4:
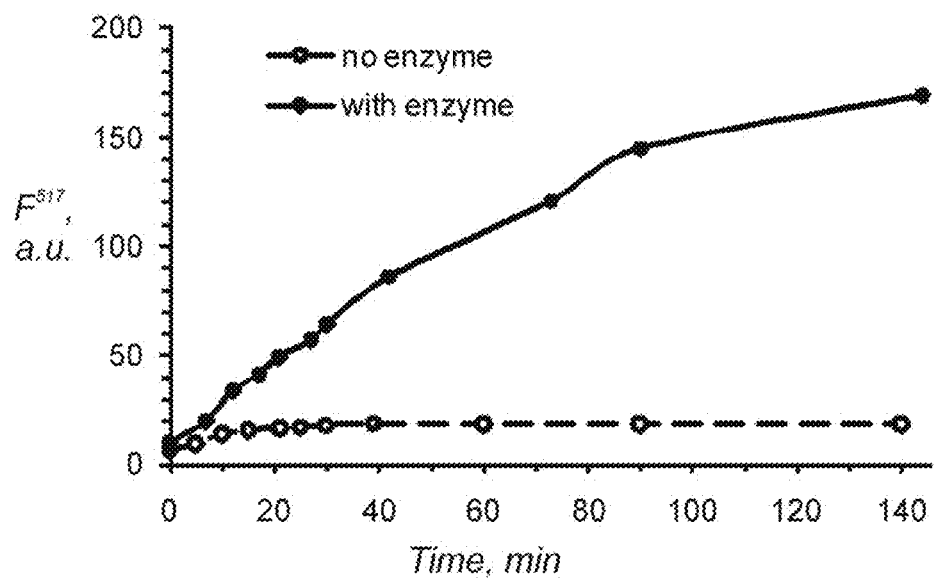
FIG. 4 is a graph showing the fluorescence enhancement of Enz-BDP2 in the presence of the analyte HepC40 (SEQ ID NO.: 5) with (●) or without (○) RNase HII.

As shown in FIG. 4, fluorescence enhancement of Enz-BDP2 in the presence of the analyte HepC40 (SEQ ID NO.: 5) with or without RNase HII. Reaction conditions: 10 nM molecular beacon 2 (MB2), 100 nM BDP2 (strands α and β) 10 nM HepC40; 2U RNase HII; 20 mM Tris-HCl, pH 8.8; 10 mM $(NH_4)_2SO_4$, 10 mM KCl, 25 mM MgCl, 0.1% Triton X-100; 30° C.

Figure 5:
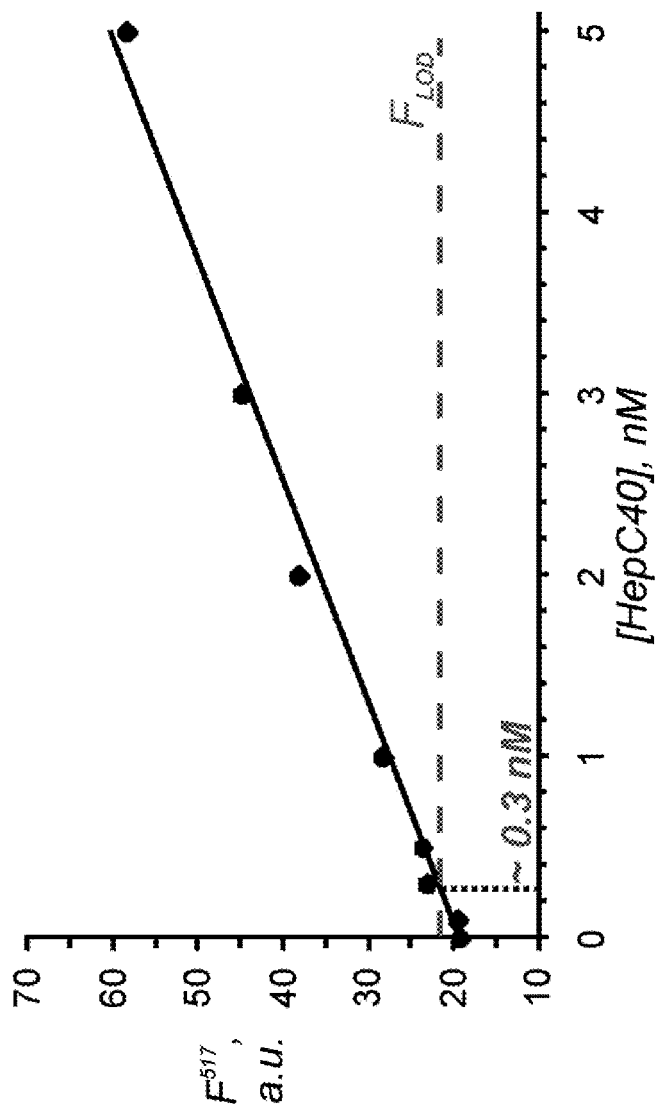
FIG. 5 is a graph showing the fluorescence enhancement of Enz-BDP2 in the presence of the analyte HepC40 (SEQ ID NO.: 5) as a function of the analyte concentration.

As shown in FIG. 5, fluorescence enhancement of Enz-BDP2 in the presence of the analyte HepC40 (SEQ ID NO.: 5) as a function of the analyte concentration. Reaction conditions: 10 nM universal molecular beacon 2 (MB2), 100 nM BDP2 (strands α and β), 0.1-5 nM HepC40; 2U RNase HII; 20 mM Tris-HCl, pH 8.8; 10 mM $(NH_4)_2SO_4$, 10 mM KCl, 25 mM MgCl, 0.1% Triton X-100; 30° C., for 1 h.

Example 4

Figure 12:
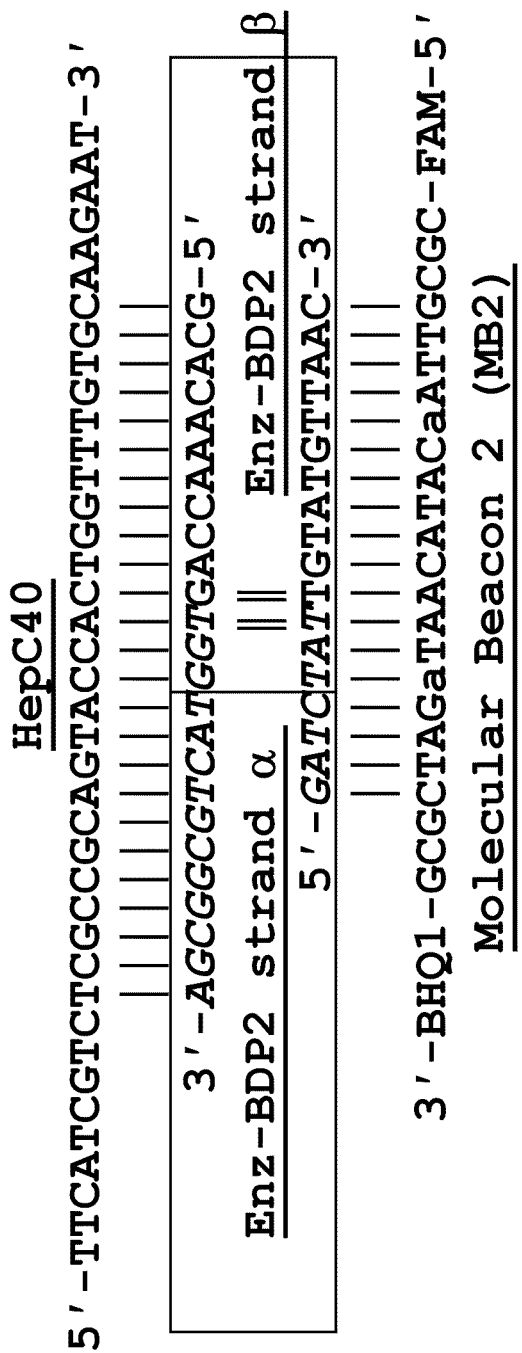
FIG. 12 illustrates the quadripartite complex formed by the binding of the Enz-MB2 strands α and β (SEQ ID NOs.: 6 and 7, respectively; strand a italicized) to a target analyte (SEQ ID NO.: 5) of the HepC40 virus and to a reporter oligonucleotide (SEQ ID NO.: 8). Small case letters indicate ribonucleotides in the reporter oligonucleotide (MB2).

RNase H-based binary probe assay: In this embodiment of the assay, the reporter oligonucleotide molecular beacon contains one or more ribonucleotides between the fluorophore and quencher attachment sites, as shown in FIGS. 6 and 12. The quadripartite complex thus formed contains a DNA-RNA hybrid (circled) that is the substrate of RNase HII. The enzyme cleaves the reporter oligonucleotide substrate, thereby releasing the fluorophore into solution. The single stranded oligonucleotide molecular beacon cannot be cleaved by RNase HII, which contributes to desirable low background fluorescence.

Furthermore, the oligonucleotide molecular beacon can form stem-loop hairpin structure to minimize its interactions with strands α and β in the absence of the analyte. This assay is adoptable to microarray format as described below.

Example 5

Restriction endonuclease-based binary probe assay: This embodiment takes advantage of recognition and cleavage of specific DNA sequences by restriction endonucleases. The restriction site-forming sequences are included in the reporter oligonucleotide and in the oligonucleotide-binding arm of strands α, β, or both α and β. As shown in FIG. 3, more than one such sequence can be included in the reporter oligonucleotide. Since restriction endonucleases do not recognize single stranded nucleic acid regions that would be present in the reporter oligonucleotide in the absence of analyte, the reporter oligonucleotide is only cleaved when the targeted analyte is present and the oligonucleotide probes hybridize to both the reporter oligonucleotide and the analyte to form the quadripartite complex, followed by an increase in fluorescent intensity.

Furthermore, the reporter oligonucleotide can form stem-loop hairpin structure to minimize its interactions with strands α and β in the absence of the analyte. This assay is adoptable to microarray format as described below.

Example 6

Exonuclease-based assay: The reporter oligonucleotide-cleaving enzyme can be an exonuclease that removes a 5' or 3'-end nucleotide. The reporter oligonucleotide will include a fluorophore and/or a quencher on 3' or 5' ends. FIG. 7 schematically illustrates a fluorophore dye conjugated with either 3' or 5' of the reporter oligonucleotide. When the quadripartite complex is formed (FIG. 7B) in the presence of the analyte, an exonuclease can cleave off the fluorophore-conjugated nucleotide, resulting in an increase in fluorescence emission.

Furthermore, the reporter oligonucleotide can form stem-loop hairpin structure to minimize its interactions with strands α and β in the absence of the analyte. This assay is adoptable to microarray format as described below.

Example 7

Figure 8:
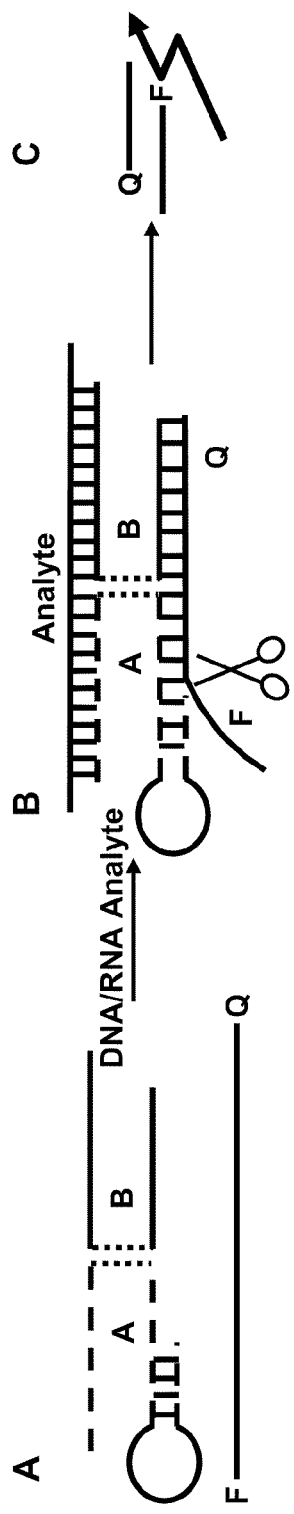
FIG. 8 is a scheme showing a flap structure-forming probe.
Figure 9:
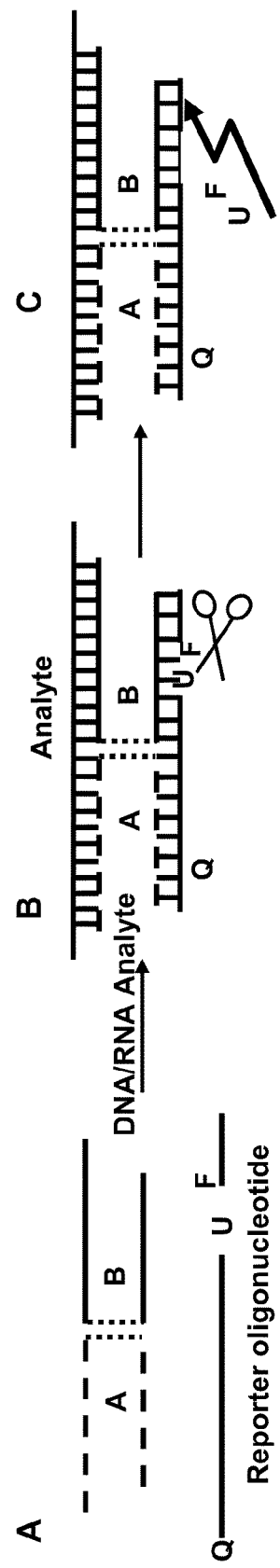
FIG. 9 is a scheme showing a glycosylase-based probe assay. The damaged or mismatch-forming fluorophore-labeled nucleotide is indicated as $U^F$.

Flap endonuclease-based assay: One of the oligonucleotide probe strands (strand α in FIG. 8) can contain a stem-loop structure resulting in the formation of an overhang structure, a "flap structure", in quadripartite complex formed in the presence of a target analyte (as shown in FIG. 8. Such a structure is a specific substrate for Flap-endonuclease-1 (FEN-1) that cleaves a phosphodiester bond thereby liberating the fluorophore nucleotide.

Furthermore, the oligonucleotide molecular beacon can form stem-loop hairpin structure to minimize its interactions with strands α and β in the absence of the analyte. This assay is adoptable to microarray format as described below.

Example 8

DNA glycosylase-based assay: In this assay the oligonucleotide molecular beacon has at least one irregular or mismatched-forming nucleotide (indicated as $U^F$ in FIG. 9). This nucleotide is conjugated with a fluorophore. The fluorescence of the fluorophore is quenched by the closely located quencher moiety. Upon quadripartite complex formation, however, the double stranded fragment with the embedded "damaged" nucleotide is recognized by a specific DNA glycosylase. Upon hydrolysis of the N-glucosidic bond (FIG. 9): the fluorescently-labeled nucleotide base is released into solution. Possible glycosylases include, but are not limited to, uracil DNA glycosylases, 8-oxoguanine DNA glycosylase, 3-methyadenine DNA glycosylas, T:G miss-pair DNA glycosylase, and the like.

Furthermore, the reporter oligonucleotide can form stem-loop hairpin structure to minimize its interactions with strands α and β in the absence of the analyte. This assay is adoptable to microarray format as described below.

Example 9

Microarrays of enzyme assisted binary probes: The systems of the disclosure can be adapted to the solid-support based formats such as microarrays. In microarrays, one of the oligonucleotide probes can be attached to the surface of a solid support, while a second strand and the analyte will be added in solution, hybridized with the solid-support bound strand, followed by treatment with a specific DNA processing enzyme.

For example, as schematically shown in FIG. 10, a DNA glycosylase-based assay according to Example 8 can be converted to the microarray format. FIG. 10 shows microarray features, each of which contains covalently attached one strand of the binary probe (strand a in FIG. 10). The analyte and strand β are incubated with the microarray in the presence of the reporter oligonucleotide. The reporter oligonucleotide contains damages or mismatch-forming nucleotide(s) conjugated with the quencher dye. When the quadripartite complex is formed, the specific DNA glycosylase can be added to the microarray and cleaves off the quencher conjugated bases. The remaining quadripartite complex emits bright fluorescence, which can be detected by a conventional fluorescent scanner.

Example 10

Deoxyribozyme assisted probe system: This type of probe is related to enzyme-assisted probes, although the protein enzyme is not required. The absence of a protein enzyme reduces cost of the assay, and makes the assay system more stable with a longer shelf-life.

In this embodiment of the probe system, at least one of the oligonucleotide probes binding to the target analyte contains a deoxyribozyme sequence embedded in the oligonucleotide molecular beacon-binding arm.

Figure 13:
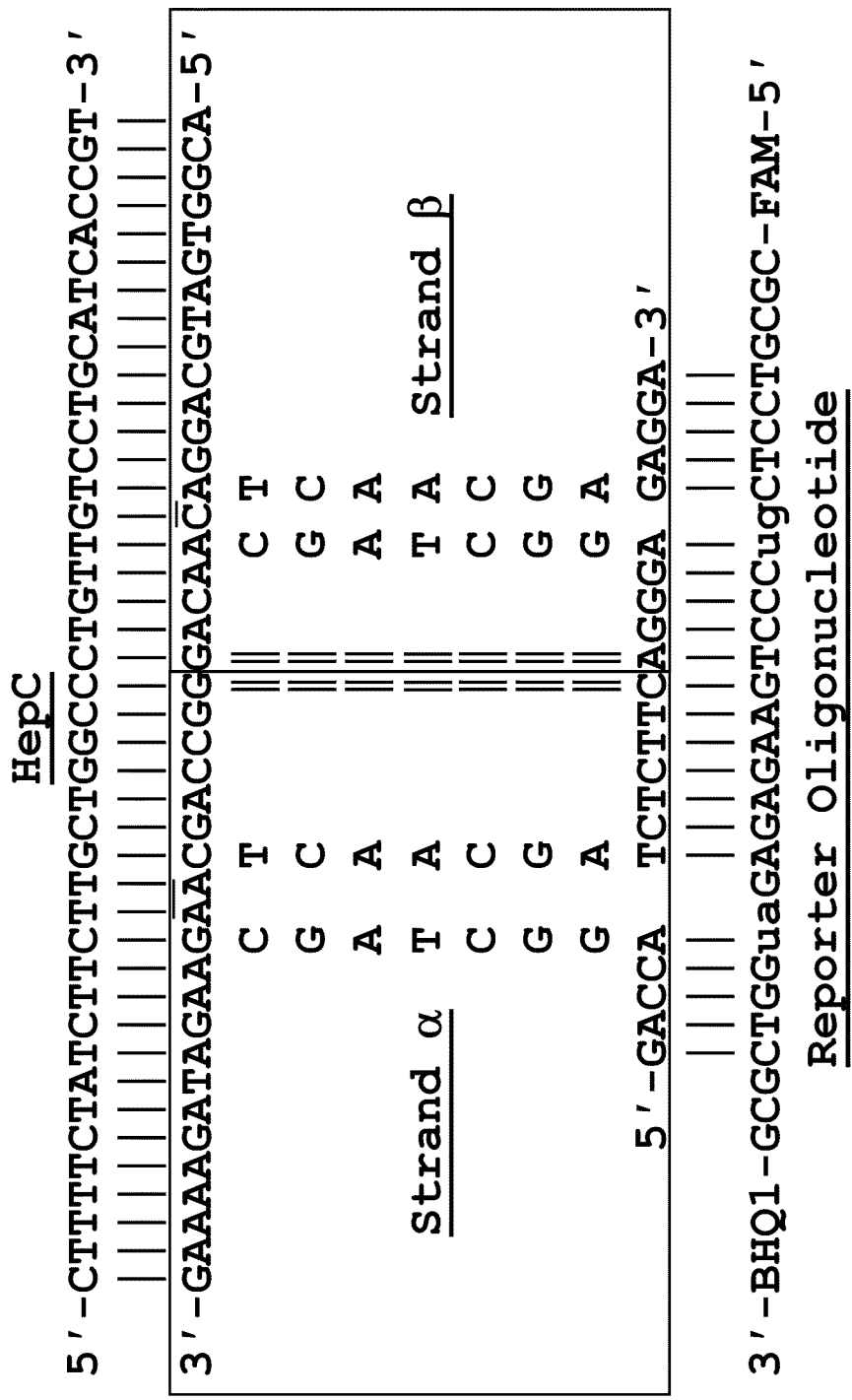
FIG. 13 illustrates the quadripartite complex formed by the binding of α and β strand oligonucleotide probes (SEQ ID NOS.: 10 and 11, respectively) to a target analyte (SEQ ID NO.: 9) of the HepC virus and to a reporter oligonucleotide (SEQ ID NO.: 12). Each of the α and the β strands includes a region, the sequence of which forms a deoxyribozyme. In this embodiment of a quadripartite complex, each of the strands encodes a different deoxyribozyme and each is located opposite a cleavable ribonucleotide of the reporter oligonucleotide. Small case letters indicate ribonucleotides in the reporter oligonucleotide.

Presence of the specific nucleic acid analyte results in the formation of a quadripartite complex (FIG. 11) in which the deoxyribozyme binds opposite the cleavable site (X) in the reporter oligonucleotide. The cleavage of the reporter oligonucleotide leads to separation of fluorophore and the quencher, thus generating high fluorescent signal. In the example illustrated in FIG. 13, the two oligonucleotides of the binary probe independently encode different deoxyribozymes.

---

SEQUENCE LISTING

```
<160> NUMBER OF SEQ ID NOS: 12

<210> SEQ ID NO 1
<211> LENGTH: 28
<212> TYPE: DNA
<213> ORGANISM: Artificial sequence
<220> FEATURE:
<223> OTHER INFORMATION: HepC30 fragment analyte

<400> SEQUENCE: 1
tgccccggag gtctgtagac cgtgcacc                                          28

<210> SEQ ID NO 2
<211> LENGTH: 21
<212> TYPE: DNA
<213> ORGANISM: Artificial sequence
<220> FEATURE:
<223> OTHER INFORMATION: Enz-BDP1 strand alpha

<400> SEQUENCE: 2
gaccatctca gacctcccgg g                                                 21

<210> SEQ ID NO 3
<211> LENGTH: 20
<212> TYPE: DNA
<213> ORGANISM: Artificial sequence
<220> FEATURE:
<223> OTHER INFORMATION: Enz-BDP1 strand beta

<400> SEQUENCE: 3
cacggtctac gttcctatag                                                   20

<210> SEQ ID NO 4
<211> LENGTH: 28
<212> TYPE: DNA
<213> ORGANISM: Artificial sequence
<220> FEATURE:
<223> OTHER INFORMATION: Molecular Beacon 1 (MB1) conjugated to
      fluorescein and Black Hole Quencher 1 and N is ribonucleotide A
<220> FEATURE:
<221> NAME/KEY: misc_feature
<222> LOCATION: (13)..(13)
<223> OTHER INFORMATION: n is ribonucleotide a
```

```
<400> SEQUENCE: 4
ccgactcact atnggaagag atggtcgg                                          28

<210> SEQ ID NO 5
<211> LENGTH: 40
<212> TYPE: DNA
<213> ORGANISM: Artificial sequence
<220> FEATURE:
<223> OTHER INFORMATION: HepC40 fragment analyte

<400> SEQUENCE: 5
ttcatcgtct cgccgcagta ccactggttt gtgcaagaat                             40

<210> SEQ ID NO 6
<211> LENGTH: 21
<212> TYPE: DNA
<213> ORGANISM: Artificial sequence
<220> FEATURE:
<223> OTHER INFORMATION: Enz-BDP2 strand alpha

<400> SEQUENCE: 6
gatctattgg tactgcggcg a                                                 21

<210> SEQ ID NO 7
<211> LENGTH: 22
<212> TYPE: DNA
<213> ORGANISM: Artificial sequence
<220> FEATURE:
<223> OTHER INFORMATION: Enz-BDP2 strand beta

<400> SEQUENCE: 7
gcacaaacca gtgtatgtta ac                                                22

<210> SEQ ID NO 8
<211> LENGTH: 24
<212> TYPE: DNA
<213> ORGANISM: Artificial sequence
<220> FEATURE:
<223> OTHER INFORMATION: Molecular beacon 2 (MB2) conjugated to
      fluorescein and BHQ-1 (Nis ribonucleotide A)
<220> FEATURE:
<221> NAME/KEY: misc_feature
<222> LOCATION: (8)..(8)
<223> OTHER INFORMATION: n is ribonucleotide a
<220> FEATURE:
<221> NAME/KEY: misc_feature
<222> LOCATION: (17)..(17)
<223> OTHER INFORMATION: n is ribonucleotide a

<400> SEQUENCE: 8
cgcgttanca tacaatngat cgcg                                              24

<210> SEQ ID NO 9
<211> LENGTH: 42
<212> TYPE: DNA
<213> ORGANISM: Artificial sequence
<220> FEATURE:
<223> OTHER INFORMATION: HepC fragment analyte

<400> SEQUENCE: 9
cttttctatc ttcttgctgg ccctgttgtc ctgcatcacc gt                          42

<210> SEQ ID NO 10
<211> LENGTH: 48
<212> TYPE: DNA
<213> ORGANISM: Artificial sequence
```

```
<220> FEATURE:
<223> OTHER INFORMATION: strand alpha

<400> SEQUENCE: 10
gaccaggcta gctcaacgat ctcttcggcc agcaagaaga tagaaaag                48

<210> SEQ ID NO 11
<211> LENGTH: 44
<212> TYPE: DNA
<213> ORGANISM: Artificial sequence
<220> FEATURE:
<223> OTHER INFORMATION: strand beta

<400> SEQUENCE: 11
acggtgatgc aggacaacag agggaggcta gctcaacgag agga                    44

<210> SEQ ID NO 12
<211> LENGTH: 32
<212> TYPE: DNA
<213> ORGANISM: Artificial sequence
<220> FEATURE:
<223> OTHER INFORMATION: Molecular Beacon conjugated to FAM and BHQ1
      (where in cnnc, nn are ribonucleotides gu, and in gnng, nn are
      ribonucleotides au)
<220> FEATURE:
<221> NAME/KEY: misc_feature
<222> LOCATION: (10)..(11)
<223> OTHER INFORMATION: nn is ribonucleotide pair gu;
<220> FEATURE:
<221> NAME/KEY: misc_feature
<222> LOCATION: (24)..(25)
<223> OTHER INFORMATION: nn is ribonucleotide pair au;

<400> SEQUENCE: 12
cgcgtcctcn ncctgaaga gagnnggtcg cg                                  32
```

We claim:

1. A system for detecting a target analyte, the system comprising:
   (a) a first oligonucleotide probe comprising: (i) at the 5'-terminus thereof, a reporter oligonucleotide-binding arm having a nucleotide sequence complementary to the nucleotide sequence of a first region of a reporter oligonucleotide; and (ii) at the 3'-terminus thereof, an analyte-binding arm having a nucleotide sequence characterized as selectively binding to a first region of a target analyte;
   (b) a second oligonucleotide probe comprising: (i) at the 3'-terminus thereof, a reporter oligonucleotide-binding arm having a nucleotide sequence complementary to the nucleotide sequence of a second region of a reporter oligonucleotide; and (ii) at the 5'-terminus thereof, an analyte-binding arm having a nucleotide sequence characterized as selectively binding to a second region of a target analyte;
   (c) a reporter oligonucleotide comprising: (i) a first region having a nucleotide sequence complementary to the reporter oligonucleotide-binding arm of the first oligonucleotide probe; (ii) a second region having a nucleotide sequence complementary to the reporter oligonucleotide-binding arm of the second oligonucleotide probe; (iii) a fluorophore and a quencher disposed on the reporter oligonucleotide whereby said fluorophore and quencher interact in the absence of a target analyte to quench fluorescence generated by the fluorophore; and (iv) a cleavable site disposed between the fluorescent label and the quencher, wherein the cleavable site is characterized as cleavable by a protein enzyme; and
   wherein the target analyte, the first and second oligonucleotide probes, and the reporter oligonucleotide form a quadripartite complex, thereby providing a configuration of the cleavable site of the reporter oligonucleotide allowing said site to be cleaved by the protein enzyme.

2. The system of claim 1, wherein a cleavable site of the reporter oligonucleotide comprises a ribonucleotide.

3. The system of claim 1, wherein the reporter oligonucleotide-binding arm of at least one oligonucleotide probe comprises a nucleotide sequence that provides a site in the reporter oligonucleotide specifically cleavable by a restriction endonuclease when said oligonucleotide probe is hybridized to the reporter oligonucleotide, and the oligonucleotide-cleaving agent is said restriction endonuclease.

4. The system of claim 1, wherein the protein enzyme is selected from the group consisting of: a restriction endonuclease, an RNase H, a Flap-endonuclease-1 (FEN-1), and a DNA glycosylase.

5. The system of claim 1, wherein at least one of the first oligonucleotide probe and the second oligonucleotide probe further comprises a linker connecting the analyte-binding arm and the reporter oligonucleotide-binding arm of said oligonucleotide probe.

6. The system of claim 1, wherein the reporter oligonucleotide is a molecular beacon characterized as having a stem-loop configuration in the absence of a target analyte.

7. The system of claim 1, wherein at least one of the fluorophore and the quencher is attached to the reporter oligonucleotide at the 5' or the 3' terminus thereof.

8. The system of claim 1, wherein the nucleotide sequences of the analyte-binding arms of the first and the second oligonucleotide probes are independently selected to specifically bind to a target analyte comprising a deoxyribonucleotide sequence, a ribonucleotide sequence, a double-stranded nucleic acid, a peptide, a polypeptide, or a variant thereof.

9. The system of claim 1, wherein the first or the second oligonucleotide probe is tethered to a substrate.

10. The system of claim 1, further comprising a plurality of oligonucleotide probe pairs, each probe pair comprising a first oligonucleotide probe and a second oligonucleotide probe.

11. The system of claim 10, wherein one oligonucleotide probe in each probe pair is tethered to a substrate.

12. The system of claim 11, wherein the oligonucleotide probe in each probe pair of the plurality of oligonucleotide probes is disposed on the substrate as an array.

13. A method of identifying a target analyte in a test sample, the method comprising the steps of:
  (i) forming a reaction mix by combining the test sample with:
    (a) a first oligonucleotide probe comprising: (i) at the 5'-terminus thereof, a reporter oligonucleotide-binding arm having a nucleotide sequence complementary to the nucleotide sequence of a first region of a reporter oligonucleotide; and (ii) at the 3'-terminus thereof, an analyte-binding arm having a nucleotide sequence characterized as selectively binding to a first region of a target analyte;
    (b) a second oligonucleotide probe comprising: (i) at the 3'-terminus thereof, a reporter oligonucleotide-binding arm having a nucleotide sequence complementary to the nucleotide sequence of a second region of a reporter oligonucleotide; and (ii) at the 5'-terminus thereof, an analyte-binding arm having a nucleotide sequence characterized as selectively binding to a second region of a target analyte;
    (c) a reporter oligonucleotide comprising: (i) a first region having a nucleotide sequence complementary to the reporter oligonucleotide-binding arm of the first oligonucleotide probe; (ii) a second region having a nucleotide sequence complementary to the reporter oligonucleotide-binding arm of the second oligonucleotide probe; (iii) a fluorophore and a quencher disposed on the reporter oligonucleotide whereby said fluorophore and quencher interact in the absence of a target analyte to quench fluorescence generated by the fluorophore; and (iv) a cleavable site disposed between the fluorescent label and the quencher, wherein the cleavable site is characterized as cleavable by a protein enzyme or a region of the first, and
  (ii) incubating the reaction mix under conditions suitable for the formation of a quadripartite complex between the analyte-binding arms of the first and the second oligonucleotide probes, the target analyte in the test sample, and the reporter oligonucleotide, thereby exposing a cleavable site of the reporter oligonucleotide for cleavage;
  (iii) cleaving at the cleavable site of the reporter oligonucleotide with the protein enzyme, thereby releasing the fluorophore, the quencher, or both the fluorophore and the quencher, from the quadripartite complex;
  (iv) illuminating the reaction mix at a wavelength suitable for inducing a fluorescent emission by the fluorophore; and
  (v) detecting the fluorescence emitted by the fluorophore, thereby detecting the presence of the target analyte in the test sample.

14. A kit comprising:
  (a) a first oligonucleotide probe comprising: (i) at the 5'-terminus thereof, a reporter oligonucleotide-binding arm having a nucleotide sequence complementary to the nucleotide sequence of a first region of a reporter oligonucleotide; and (ii) at the 3'-terminus thereof, an analyte-binding arm having a nucleotide sequence characterized as selectively binding to a first region of a target analyte;
  (b) a second oligonucleotide probe comprising: (i) at the 3'-terminus thereof, a reporter oligonucleotide-binding arm having a nucleotide sequence complementary to the nucleotide sequence of a second region of a reporter oligonucleotide; and (ii) at the 5'-terminus thereof, an analyte-binding arm having a nucleotide sequence characterized as selectively binding to a second region of a target analyte;
  (c) a reporter oligonucleotide comprising: (i) a first region having a nucleotide sequence complementary to the reporter oligonucleotide-binding arm of the first oligonucleotide probe; (ii) a second region having a nucleotide sequence complementary to the reporter oligonucleotide-binding arm of the second oligonucleotide probe; (iii) a fluorophore and a quencher disposed on the reporter oligonucleotide whereby said fluorophore and quencher interact in the absence of a target analyte to quench fluorescence generated by the fluorophore; and (iv) a cleavable site disposed between the fluorescent label and the quencher, wherein the cleavable site is characterized as cleavable by a protein enzyme, and wherein one oligonucleotide probe in each probe pair optionally is tethered to a substrate, and optionally disposed on the substrate as an array; wherein the target analyte, the first and second oligonucleotide probes, and the reporter oligonucleotide form a quadripartite complex, thereby providing a configuration of the cleavable site of the reporter oligonucleotide allowing said site to be cleaved by the protein enzyme; and
  (d) optionally, packaging and instructions for the use of the kit to detect a target analyte in a test sample.

15. The kit of claim 14, further comprising a plurality of oligonucleotide probe pairs, each probe pair comprising a first oligonucleotide probe and a second oligonucleotide probe.

16. The kit of claim 15, wherein one oligonucleotide probe in each probe pair is tethered to a substrate.

17. The kit of claim 16, wherein the oligonucleotide probe in each probe pair of the plurality of oligonucleotide probes is disposed on the substrate as an array.

* * * * *